United States Patent
Liu et al.

(10) Patent No.: US 6,511,938 B1
(45) Date of Patent: Jan. 28, 2003

(54) ALKYLENE OXIDE CATALYSTS HAVING ENHANCED ACTIVITY AND/OR STABILITY

(75) Inventors: Albert Cheng-Yu Liu, Charleston, WV (US); Erlind Magnus Thorsteinson, Charleston, WV (US); Hwaili Soo, Charleston, WV (US); James Herndon McCain, Charleston, WV (US); David Michael Minahan, Cross Lanes, WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 1055 days.

(21) Appl. No.: 08/619,216

(22) Filed: Mar. 21, 1996

Related U.S. Application Data

(63) Continuation of application No. 08/385,729, filed on Feb. 8, 1995, now abandoned, which is a continuation of application No. 08/156,872, filed on Nov. 19, 1993, now abandoned, which is a continuation of application No. 08/070,021, filed on May 28, 1993, now abandoned, which is a continuation of application No. 07/856,853, filed on Mar. 24, 1993, now abandoned, which is a continuation of application No. 07/596,241, filed on Oct. 12, 1990, now abandoned.

(51) Int. Cl.$^7$ .................................................. B01J 23/50
(52) U.S. Cl. ....................... 502/347; 502/325; 502/326; 502/330; 502/344
(58) Field of Search ................................. 502/325, 326, 502/330, 347, 344

(56) References Cited

U.S. PATENT DOCUMENTS

| | | | | |
|---|---|---|---|---|
| 2,040,782 A | | 5/1936 | Van Peski | 260/54 |
| 2,279,469 A | * | 4/1942 | Law et al. | 549/534 |
| 2,605,239 A | | 7/1952 | Sears, Jr. | 252/475 |
| 2,615,899 A | | 10/1952 | Sears | 260/348.5 |
| 2,615,900 A | | 10/1952 | Sears, Jr. | 260/348.5 |
| 3,758,418 A | | 9/1973 | Leonard et al. | 252/464 |
| 3,844,981 A | | 10/1974 | Cusumano | 252/471 |
| 4,007,135 A | | 2/1977 | Hayden et al. | 252/467 |
| 4,248,740 A | | 2/1981 | Mitsuhata et al. | 252/463 |
| 4,717,703 A | | 1/1988 | Cognion et al. | 502/348 |
| 4,774,222 A | * | 9/1988 | Rashkin | 502/347 |
| 4,897,376 A | | 1/1990 | Liu | 502/347 |
| 4,908,343 A | | 3/1990 | Bhasin | 502/218 |
| 5,112,795 A | | 5/1992 | Minahan et al. | 502/324 |
| 5,407,888 A | | 4/1995 | Herzog et al. | 502/344 |

* cited by examiner

*Primary Examiner*—Nadine G. Norton
(74) *Attorney, Agent, or Firm*—Gus Hampilos; Tai-Sau Choo

(57) ABSTRACT

Catalysts for the production of alkylene oxide by the epoxidation of alkene with oxygen comprise a silver-containing support, and a sufficient amount of cobalt component to enhance at least one of activity and/or efficiency and/or stability as compared to a similar catalyst which does not contain cobalt component.

8 Claims, No Drawings

ALKYLENE OXIDE CATALYSTS HAVING ENHANCED ACTIVITY AND/OR STABILITY

This application is a Continuation of prior U.S. application: Ser. No. 08/385,729 filing date Feb. 8, 1995, now abandoned and/which is a continuation of application Ser. No. 08/156,872 filing date Nov. 19, 1993, now abandoned and/which is a continuation of application Ser. No. 08/070,021 filing date May 28, 1993, now abandoned, and/which is a continuation of application Ser. No. 07/856,853 filing date Mar. 24, 1993, now abandoned, and/which is a continuation of application Ser. No. 07/596,241 filing date Oct. 12, 1990, now abandoned.

FIELD OF THE INVENTION

This invention relates to silver-containing, supported catalysts for the epoxidation of alkene, especially ethylene, to the corresponding alkylene oxide, e.g., ethylene oxide, which contain a stability and/or efficiency and/or activity enhancing amount of a cobalt-containing component.

BACKGROUND TO THE INVENTION

Ethylene oxide is commercially produced by the epoxidation of ethylene over silver-containing catalyst at elevated temperature. Considerable research efforts have been devoted to providing catalysts that increase the efficiency, or selectivity, of the process to ethylene oxide.

The manufacture of ethylene oxide by the reaction of oxygen or oxygen-containing gases with ethylene in the presence of a silver catalyst is an old and developed art. For example, U.S. Pat. No. 2,040,782, patented May 12, 1936, describes the manufacture of ethylene oxide by the reaction of oxygen with ethylene in the presence of silver catalysts which contain a class of metal-containing promoters. In Reissue U.S. Pat. No. 20,370, dated May 18, 1937, Leforte discloses that the formation of olefin oxides may be effected by causing olefins to combine directly with molecular oxygen in the presence of a silver catalyst. From that point on, the prior art has focused its efforts on improving the catalyst's efficiency in producing ethylene oxide.

In characterizing this invention, the terms "conversion", "selectivity", and "yield" are employed as defined in U.S. Pat. No. 3,420,784, patented Jan. 7, 1969, at column 3, lines 24–35 inclusive. This definition of "selectivity" is consistent with that disclosed in U.S. Pat. No. 2,766,261 at column 6, lines 5–22, and U.S. Pat. No. 3,144,916, lines 58–61. The definitions of "yield" and "conversion" have more varied meaning in the art and are not to be employed as defined, for example, in the aforementioned U.S. Pat. No. 2,766,261. The terms "efficiency" and "selectivity", as used throughout the specification and claims are intended to be synonymous.

Silver catalysts employed in the manufacture of ethylene oxide have undergone significant changes since their initial period of development. As reported by the art, silver particles were first deposited upon support materials with little attention being paid to support properties, such as surface area, pore volume and chemical inertness. As the art evolved, there developed special technologies related to carriers or supports containing silver that were more effective for the reaction of ethylene with oxygen to produce ethylene oxide. Today, most supports for the silver catalysts are shaped particulate materials which can be loaded in the interior of a reactor wherein the reacting gases and the gaseous products of the reaction are capable of flowing in and about these particulate materials to pass through the reactor and be recovered. The size and shape of the support are variable factors and the particular size and shape selected are peculiar to the reactor employed, the gas flow required, and the pressure drop across the reactor, with other factors also being considered.

The carriers that have been employed are typically made of inorganic materials, generally of a mineral nature. In most cases, the preferred carrier is made of alpha-alumina, such as has been described in the patent literature: see for example, U.S. Pat. Nos. 2,294,383; 3,172,893; 3,332,887; 3,423,328; and 3,563,914.

The carriers which are employed for the manufacture of most, if not all, commercially employed ethylene oxide catalysts are produced by companies who do not produce such catalysts. As a rule, the methods of making such carriers are trade secrets of significant value to the carrier manufacturers. Consequently, the catalyst manufacturer cannot know how the carrier is made. Critical to making a carrier which proves uniquely desirable for the manufacture of a successful catalyst can be a number of factors, such as the purity and other physical/chemical properties of raw materials used to make the carrier and the method by which the carrier is made.

The silver that is deposited on these carriers is thought to be in the form of small particles because that is all that can be seen by current microscopic techniques. The patent literature indicates that the size of the silver is a factor in the effectiveness of the catalyst and in most cases fine particle silver is obtained utilizing the standard processes in the art; see, for example, U.S. Pat. Nos. 2,554,459; 2,831,870; 3,423,328 (specifies that silver particles of 150–400 Angstroms are employed); U.S. Pat. No. 3,702,259 (disclosed a preparation procedure for forming silver particles less than 1 micron in diameter) and U.S. Pat. No. 3,758,418 (discloses silver particles having a diameter less than 1000 Angstroms). Improvements in microscopic examinations of silver catalysts enable the observation that the particle size ranges to even smaller values.

The deposition of silver onto the carrier can be achieved by a number of techniques but the two techniques which are most frequently employed involve, in one case, the impregnation of the support with a silver solution followed by heat treatment of the impregnated support to effect deposition of the silver on the support and, in the other case, the coating of the silver on the support by the precipitation of silver or the preformation of silver into a slurry such that the silver particles are deposited on the support and adhere to the support surface when the carrier or support is heated to remove the liquids present. These various procedures are exemplified in various U.S. Patents such as U.S. Pat. Nos. 2,773,844; 3,207,700; 3,501,407; 3,664,970 (see British Patent 754,593) and U.S. Pat. No. 3,172,893.

The surface area provided by the support has been the subject of considerable interest in the development of silver catalysts. Disclosures concerning the surface area of the catalyst carrier can be found in U.S. Pat. No. 2,766,261 (which discloses that a surface area of 0.002–10 $m^2/gm$ is suitable); U.S. Pat. No. 3,172,893 which depicts a porosity of 35–65% and a pore diameter of 80–200 microns); U.S. Pat. No. 3,725,307 which depicts a surface area of less than 1 sq.m/gm and an average pore diameter of 10–15 microns); U.S. Pat. No. 3,664,970 (which utilizes a support having a minimum porosity of about 30%, at least 90% of the pores having diameters in the range of 1–30 microns, and the average of such diameters being in the range of 4–10 microns); and U.S. Pat. No. 3,563,914 which utilizes a catalyst support having a surface area of less than 1 sq.

m/gm, a volume of 0.23 ml/gm and a particle size between 0.074 and 0.30 mm). Low surface area, inert alpha-alumina is favored by the prior art.

It has been known for a long time that impurities present in the catalyst and/or the gas phase can materially impact upon the reaction. In the early development of the art, there were no techniques available for identifying or measuring such impurities. Consequently, one could not isolate the role that such impurities played. However, even in the earliest periods of the development of the art, the use of alkali metals as promoters for the silver catalyzed production of ethylene oxide was extremely well known in the art. U.S. Pat. No. 2,177,361, issued October 1939, has a teaching of the use of alkali metals in silver catalysts. U.S. Pat. No. 2,238,471 discloses that lithium is very desirable as a promoter but that potassium and cesium are detrimental when used in amounts of essentially 10% by weight of potassium hydroxide or cesium hydroxide to the silver oxide employed in making the catalyst. Later, U.S. Pat. No. 2,404,438 states that sodium and lithium are effective promoters for this reaction. Essentially the same teaching can be found in U.S. Pat. No. 2,424,084. U.S. Pat. No. 2,424,086 generalizes about alkali metals as promoters and specifies sodium in particular. In U.S. Pat. No. 2,671,764 (the Sacken sulfate patent), the patentees believe that alkali metals in the form of their sulfates are effective as promoters for such silver catalysts. In particular, the patentees state that sodium, potassium, lithium, rubidium or cesium sulfates may be used as promoters.

U.S. Pat. No. 2,765,283 describes the pretreatment of a support with a dilute solution of a chlorine-containing compound and indicates that such chlorine compounds should be inorganic. Particular illustrations cited of suitable inorganic chlorine compounds included sodium chloride, lithium chloride and potassium chlorate. This patent specifies that the amount of the inorganic chlorine-containing compound which is deposited on the catalyst support is from 0.0001% to 0.2% by weight based on the weight of the support. U.S. Pat. No. 2,615,900 to Sears describes the use of metal halide in the treatment of the supported catalyst and specifies that such halides can be of alkali metals such as lithium, sodium, potassium and cesium. The metal halide is present in the range of 0.01% to 50% based upon the weight of metallic silver. The patent also specifies that mixtures of the individual metal halides generally classified in the patent may be used to advantage to enhance the break-in period of a new catalyst composition while at the same time maintaining a moderate but steady activity of the catalyst over an extended period of time during normal operation. Thus, one particular metal halide treated catalyst would provide a short-term high initial activity whereas another of the metal halides would provide a longer term moderate activity for the catalyst. This patent takes the position that the metal halides which are provided in the catalyst serve to inhibit the combustion of ethylene to carbon dioxide and thus classifies these materials as catalyst depressants or anticatalytic materials.

U.S. Pat. No. 2,709,173 describes the use of a silver catalyst for making ethylene oxide in which there are provided simultaneously with the introduction of silver to the solid support, any of the alkali metal halides such as lithium, sodium, potassium, and rubidium compounds of chlorine, bromine and iodine, to enhance the overall production of ethylene oxide. The patent specifies small amounts "of less than about 0.5% are desirable." In particular, the patent emphasizes "proportions of alkali metal halide within the range of about 0.0001 to about 0.1%" are most preferred. The patent states that "although the preferred catalyst composition contains a separate promoter it is not always necessary since during preparation of the catalyst the alkali metal halide may be converted to some extent to the corresponding alkali metal oxide which acts as a promoter." U.S. Pat. No. 2,766,261 appears to draw from the teachings of U.S. Pat. No. 2,238,474 in that cesium and potassium are said to be detrimental in silver catalysts; sodium and lithium are suggested as useful promoters. However, U.S. Pat. No. 2,769,016 finds that sodium, potassium and lithium are promoters when used in the silver catalysts. This latter patent also recommends the pretreatment of the support with dilute solutions of sodium chloride, lithium chloride or potassium chlorate.

U.S. Pat. No. 2,799,687 to Gould, et al., states that the addition of metal halides within the range described by Sears in U.S. Pat. No. 2,615,900 is not productive of optimum results. This is said to be especially true in the case of alkali metal halides, particularly the chloride and fluoride of sodium and potassium. The patentees recommend that the inorganic halide component of the catalyst be maintained within the range of 0.01–5 weight percent, preferably 0.01 to 0.1 weight percent, based on the weight of the "silver oxidative catalytic component," i.e., the silver salt transformed into elemental silver. U.S. Pat. No. 3,144,416 mentions a variety of metals as promoters and one of them is cesium. U.S. Pat. No. 3,258,433 indicates that sodium is an effective promoter. U.S. Pat. No. 3,563,913 recommends the use of alkali metals such as lithium compounds as promoters. The preferred amount of promoting material is said to be about 0.03 to 0.5%, by weight of metal oxide based on the weight of the support. U.S. Pat. No. 3,585,217 states that alkali metal chlorides "are known to counteract the formation of carbon dioxide" and "may be incorporated into the catalyst." U.S. Pat. No. 3,125,538 discloses a supported silver catalyst containing a coincidentally-deposited alkali metal selected from among potassium, rubidium and cesium in a specified gram atom ratio relative to silver. The weight of silver is preferably 2–5% by weight of the catalyst. The patentees characterize this catalyst as being especially suitable for the reaction of nitric oxide with propylene. This same catalyst is produced inherently by the processes of the examples of U.S. Pat. No. 3,702,259, as discussed previously, which patent promotes their use for making ethylene oxide. U.S. Pat. Nos. 3,962,136 and 4,012,425 also disclose that same catalyst as being useful for ethylene oxide production. U.S. Pat. No. 3,962,136 describes the coincidental deposition of alkali metal with the silver on the support, the alkali metals being present in their final form on the support in the form of an oxide in which the oxide consists of cesium, rubidium or mixtures of both, optionally combined with a minor amount of an oxide of potassium. The amount of such oxide is from about $4.0 \times 10^{-5}$ gew/kg to about $8.0 \times 10^{-3}$ gew/kg of total catalyst. U.S. Pat. No. 4,356,312 describes the use of the same catalyst. U.S. patent application Ser. No. 317,349, filed Dec. 21, 1972, which is a parent to U.S. Pat. Nos. 3,962,136 and 4,010,115 and others, contains some interesting data deserving of comment. According to example 2 which contains some comparative experiments, there is described the manufacture of a catalyst which contains 310 parts per million by weight of coincidentally-added potassium and that catalyst when employed as an ethylene oxidation catalyst was found to be inactive for the production of ethylene oxide.

U.S. Pat. No. 4,207,210 (corres. Belgium Patent 821,439, based upon British Patent Specification 1,489,335) discloses that a catalyst can be made that is equivalent to that produced in the so-called parent applications cited in U.S. Pat. Nos. 3,962,136, 4,012,425, and 4,010,115 by using a sequential procedure by which the alkali metal is supplied to the support. Thus, the criticality in the method of deposition of alkali metal in the catalyst appears doubtful in the face of that type of disclosure and the disclosure of U.S. patent Nos. 4,033,903 and 4,125,480 which describe subjecting used silver-containing catalysts to a post-addition of one or more of potassium, rubidium or cesium. Apparently, such treatment regenerates the catalyst's ability to enhance selectivity to ethylene oxide. Another patent which tends to indicate that a post-addition of alkali metal such as cesium gives results equivalent to either pre-addition or simultaneous addition is U.S. Pat. No. 4,066,575.

German offenlegungsschrift 2,640,540 discloses in its examples a silver catalyst for ethylene oxide production containing sodium and either potassium, rubidium or cesium.

Japanese Application Publication Disclosure No. 95213/75 is directed to a process for producing ethylene oxide using a catalyst composition comprising silver, barium, potassium and cesium in specified atomic ratios. Table I of this disclosure summarizes the efficiencies achieved with the various catalyst compositions of the examples.

U.S. Pat. No. 4,039,561 discloses a catalyst for preparing ethylene oxide containing silver, tin, antimony, thallium, potassium, cesium and oxygen in specified atomic ratios.

Belgium Patent No. 854,904 discloses silver catalysts containing various mixtures of sodium and cesium. U.K. Patent Application 2,002,252 (counterpart of U.S. Pat. No. 4,248,740) discloses silver catalysts including promoters containing alkali metal, alkaline earth metals, elements of groups III, IV, V and VIII of the periodic table, with the preferred promoters being compounds of barium, tin, antimony, thallium, potassium, and cesium. This patent application discloses, in Table 2, supported silver catalysts containing various mixtures of cesium and thallium, some of which additionally contain potassium or antimony. U.S. Pat. No. 4,007,135 broadly discloses (in column 2, lines 25–30) silver catalysts for alkylene oxide production containing silver "together with a promoting amount of at least one promoter selected from lithium, potassium, sodium, rubidium, cesium, copper, gold, magnesium, zinc cadmium, strontium, calcium, niobium, tantalum, molybdenum, tungsten, chromium, vanadium and barium . . . ". U.S. Pat. Nos. 3,844,981 and 3,962,285 disclose catalysts and processes for epoxidizing olefins in the presence of a multimetallic component. The catalyst in the U.S. Pat. No. 3,962, 285 patent is said to comprise a minor amount of one or more of palladium, ruthenium, rhenium, iron and platinum with a major amount of silver. The U.S. Pat. No. 3,844,981 patent discloses the preparation of the catalyst from a decomposable salt of group 7b, 1b or the iron group of group 8 of the Periodic Table of the Elements. Preferably, the salt is selected from the group of gold, copper, rhenium, manganese and iron salts. While the patentee contemplates that these metals are in the metallic state, oxidation during epoxidation conditions may occur with one or more of these metals, e.g., rhenium, to form oxyanions containing the metal.

U.S. Pat. No. 2,040,782 discloses silver-containing catalysts for the manufacture of alkylene oxides which catalysts:

"may be considerably enhanced by the admixture with the catalytic material of small quantities of other materials capable of acting as promoters. Suitable promoters, which may be used singly or in combination, include the metals such as copper, gold, iron, manganese, nickel, cobalt, cerium, thorium and zinc." (Page 2, column 1, lines 3 to 9)

U.S. Pat. No. 2,605,239 discloses the use of beryllium oxide as a promoter. Other promoter metals such as copper, aluminum, manganese, cobalt, iron, magnesium, gold, thorium, nickel, cesium and zinc are suggested. These promoter metals are to be incorporated into the catalyst by mechanical mixture or coprecipitation.

U.S. Pat. No. 2,615,900, states:

"The activity of the silver may be enhanced by inclusion in the silver catalyst of promoters such as iron, nickel, copper, gold, platinum, manganese, cobalt, cerium, thorium, zinc, and the oxides, hydroxides, and carbonates of alkali metal and alkaline earth metals." (Column 3, lines 33 to 38) Japanese patent application Kokai 78/39404 discloses a gas phase process for the epoxidation of three and four carbon atom olefins in the presence of a silver-cadmium-silicon catalyst. The patent applicant states that other components can be incorporated in the catalyst such as elements of Groups I, II, III and VIII such as cesium, copper, gold, magnesium, calcium, beryllium, barium, zinc, aluminum, lanthanum, cerium, zirconium, thorium, iron, cobalt, nickel and platinum.

U.S. Pat. No. 3,758,418 discloses catalysts prepared by a coating technique. Among the catalysts suggested in the patent are those used for the manufacture of ethylene oxide. The metals that can be deposited are said to include the catalytically active metals found in Group IIIb to Va of the Periodic Table.

Japanese patent application Kokai 89/01224047 reported by *Chemical Abstracts*, Vol. 112 (10):83303f reports a cobalt, iron or nickel catalyst containing silver as a co-catalyst for the decomposition of nitrogen oxides to molecular nitrogen without the addition of ammonia.

While improved efficiencies of conversion to ethylene oxide are desirable, the typical concomitant increase in temperature (i.e., loss of activity) can be troublesome for a commercially-viable catalyst. Commercial ethylene oxide plants are typically operated to provide a desired balance of productivity and efficiency. Less active catalysts are thus operated at higher temperatures to achieve desired productivity. However, the upper temperature range of the catalyst is limited. Consequently, catalysts that have high initial temperatures for a given conversion rate may have shorter useful lives. Not only is catalyst a major expense to the ethylene oxide plant owner, but also, the plant must be shut down for substantial periods of time to discharge the old catalyst and charge new catalyst to the typical tubular, fixed bed ethylene oxide reactors. Hence, without a useful lifetime, e.g., two years or more, the benefit of any enhanced efficiency is quickly lost in catalyst replacement costs and plant shut-down time. Thus, the activity stability and/or efficiency stability of a catalyst are important concerns in achieving a commercially viable ethylene oxide catalyst.

Cobalt has been proposed for other silver-containing catalysts. For instance, Japanese patent application Kokai 57/13691 discloses a silver-cobalt oxide-manganese dioxide catalyst for ozone decomposition. British patent application 2,095,242 discloses a process for the oxychlorination of olefins using a catalyst comprising metallic silver and/or a compound thereof and one or more compounds of manganese, cobalt or nickel.

Methods are sought to enhance the activity and, in particular, the activity stability and/or efficiency stability of silver-containing, supported ethylene oxide catalysts which have been promoted to enhance efficiency, which while providing desirable efficiencies, are typically less active and must be operated at higher temperatures to be useful in commercial production facilities. These high temperatures can unduly shorten the catalyst life such that the catalysts are unattractive for commercial facilities. Catalysts with enhanced activity stability and/or efficiency stability would be very advantageous.

SUMMARY OF THE INVENTION

By this invention silver-containing, supported alkylene oxide catalysts suitable for the epoxidation of alkene to alkylene oxide are provided that have enhanced activity and/or efficiency and/or stability. The catalysts contain deposited thereon a sufficient amount of at least one cobalt component to increase at least one of the activity and/or efficiency and/or stability of the catalyst as compared to a similar catalyst which does not contain the cobalt component under otherwise identical conditions. Often, the cobalt component is present in an amount of at least about 10 or 20, e.g., about 25 to 1000, preferably about 50 to 500, ppm (weight) calculated as the weight of cobalt based on the total weight of the catalyst. The amount of cobalt which provides the enhanced activity and/or efficiency and/or stability generally varies depending on the nature and amounts of other components in the catalyst composition.

When the activity of a catalyst is enhanced, the temperature required to produce, under given conditions, a given level of alkylene oxide (usually expressed in terms of increase in alkylene oxide concentration across the catalyst bed) is reduced. The stability of a catalyst can be with respect to at least one of efficiency aging rate and activity aging rate. In a more stable catalyst, the efficiency aging rate and/or activity aging rate is less than that in a less stable catalyst. An especially beneficial attribute of the catalysts of this invention is an enhanced efficiency stability during the epoxidation process. By enhanced efficiency stability is meant that the selectivity of the catalyst to the production of alkylene oxide does not decrease as rapidly over time of operation as would a similar catalyst but which does not contain the cobalt component at identical operating conditions.

Preferred epoxidation systems for use of the catalysts of this invention are the systems in which the catalysts comprise at least one efficiency-enhancing salt of a redox-half reaction pair in conjunction with at least one gaseous efficiency-enhancing member of a redox-half reaction pair. In these systems, the efficiency stabilizing effect of the cobalt component is often most pronounced.

As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions.

The catalyst contains at least one other promoter in an amount sufficient to enhance the efficiency of the catalyst as compared to a similar catalyst but which does not contain the promoter. Often, the promoter comprises a compound of an element other than cobalt which is selected from Groups 1a and/or 2a and/or from Groups 3b through 7b, inclusive, and 3a through 7a, inclusive, of the Periodic Table. (References to the Periodic Table herein shall be to that as published by the Chemical Rubber Company, Cleveland, Ohio, in *CRC Handbook of Chemistry and Physics,* 46th Edition, inside back cover.) The preferred anionic promoters include the oxyanions of the elements other than oxygen having an atomic number of 5 to 83 of Groups 3b through 7b, inclusive, and 3a through 7a, inclusive, of the Periodic Table. More preferably, the promoters are one or more of the oxyanions of nitrogen, sulfur, tantalum, molybdenum, tungsten and rhenium, still more preferably one or more of the oxyanions of nitrogen, sulfur and rhenium. Many of these anionic promoters are characterized as both increasing efficiency and reducing activity of the catalysts.

In a preferred aspect of the invention, the catalyst comprises alkali metal nitrate, especially potassium and/or rubidium nitrate, especially in amounts greater than about 400 or 500 parts per million (ppm) by weight based on the weight of catalyst. In this aspect of the invention, a nitrogen and oxygen-containing compound, e.g., nitrogen oxide, nitrogen dioxide, nitrous oxide, etc., may be introduced into the reaction zone containing the catalyst as a co-promoter to enhance at least one of activity, efficiency and stability of the catalyst performance.

An aspect of this invention relates to the use of the aforementioned catalysts in epoxidizing alkene to alkylene oxide, especially ethylene to ethylene oxide.

DETAILED DISCUSSION

Alkylene oxides made using the catalysts of this invention are characterized by the structural formula

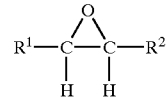

wherein $R^1$ and $R^2$ are lower alkyl, e.g., methyl or ethyl or, preferably, hydrogen. Most preferably the alkylene oxide is ethylene oxide. The alkylene oxides are made from the corresponding alkene, i.e., $R^1HC=CHR^2$. For purposes of ease of understanding, the following discussion will be made with reference to ethylene oxide and ethylene.

The catalysts of this invention are characterized by combining a sufficient amount of at least one cobalt component to enhance the activity and/or efficiency and/or stability of the catalyst as compared to a similar catalyst which does not contain the cobalt component. Although the catalysts can be used under widely varying process conditions, for purposes of determining whether sufficient cobalt component has been incorporated into the catalyst, a standard set of process conditions can be used.

The STANDARD ETHYLENE OXIDE PROCESS CONDITIONS (ABBR. "CONDITIONS") for characterizing the catalysts of this invention involve the use of a standard backmixed autoclave with full gas recycle including carbon dioxide. The CONDITIONS may be operated with some variation in ethylene, oxygen and gas phase inhibitor feed. Two cases are illustrated: air process conditions, which simulates in the backmixed reactor the typical conditions employed in commercial air-type ethylene oxide processes where air is used to supply the molecular oxygen and the oxygen process conditions, which simulates in the backmixed reactor the typical conditions in commercial oxygen-type ethylene oxide processes where molecular oxygen, as such, is employed. Each case provides a different efficiency but it is the rule for practically all cases that with air as the oxygen feed, using lower amounts of oxygen and ethylene will yield an efficiency to ethylene oxide which is about 2 to 4 percentage points lower than that when molecular oxygen is employed as oxygen feed. When the catalyst contains a redox-half reaction pair salt and is intended to be used in conjunction with the corresponding efficiency-enhancing gaseous member of a redox-half reaction pair, the CONDITIONS provide for the presence of such gaseous member. The CONDITIONS employ 2.0 mole % ethylene oxide in the outlet gas of the reactor under the following standard inlet conditions:

| Component | Air process Conditions, Mole % | Oxygen process Conditions, Mole % |
|---|---|---|
| Oxygen | 6.0 | 8.0 |
| Ethylene | 8.0 | 30 |
| Ethane | 0.5 | 0.5 |
| Carbon Dioxide | 6.5 | 6.5 |
| Nitrogen | Balance of Gas | Balance of Gas |
| Parts per million | | |
| ethyl chloride (or one-half such amount when ethylene dichloride is used) Parts per million | Optimum for Efficiency | Optimum for Efficiency |
| gaseous member of redox-half reaction pair (when required for catalyst) | Optimum for Efficiency | Optimum for Efficiency |

The CONDITIONS employ the well known backmixed bottom-agitated "Magnedrive" autoclaves described in FIG. 2 of the paper by J. M. Berty entitled "Reactor for Vapor Phase-Catalytic Studies", in *Chemical Engineering Progress,* Vol. 70, No. 5, pages 78–84, 1974.

The pressure is maintained constant at 275 psig and the total outlet flow is maintained at 22.6 SCFH. SCFH refers to cubic feet per hour at standard temperature and pressure, namely, 0° C. and one atmosphere. The outlet ethylene oxide concentration is maintained at 2.0% by adjusting the reaction temperature. Thus temperature (°C.) and catalyst efficiency are obtained as the responses describing the catalyst performance.

The catalyst test procedure used in the CONDITIONS involves the following steps:

1. 80 cc of catalyst are charged to the backmixed autoclave. The volume of catalyst is measured in a 1 inch I.D. graduated cylinder after tapping the cylinder several times to thoroughly pack the catalyst. The volume of catalyst is alternatively calculated from the packing density of the carrier and the amount of silver and additives. The weight of the catalyst is noted.

2. The backmixed autoclave is heated to about reaction temperature in a nitrogen flow of 20 SCFH with the fan operating at 1500 rpm. The nitrogen flow is then discontinued and the above-described feed stream is introduced into the reactor. The total gas outlet flow is adjusted to 22.6 SCFH. The temperature is set at 220° C.

3. The temperature is raised over the next three days to 255° C. The selectivity and the activity of the catalyst to ethylene oxide are thus obtained.

The standard deviation of a single test result reporting catalyst efficiency in accordance with the procedure described above is about 0.7% efficiency units. The standard deviation of a single test result reporting catalyst activity in accordance with the procedure described above is about 0.03 mole % ethylene oxide. The standard deviation, of course, will depend upon the quality of the equipment and precision of the techniques used in conducting the tests, and thus will vary. The test results reported herein are believed to be within the standard deviation set forth above. The running of a multiplicity of tests will reduce the standard deviation by the square root of the number of tests.

The activity stability and efficiency stability of a catalyst is conveniently determined under the CONDITIONS. The rate of decrease in activity and efficiency with time is indicative of the activity stability and efficiency stability of the catalyst. Usually, the study is conducted for about 50 days with a delta ethylene oxide concentration across the catalyst of about 2 mole percent. The time to provide an indication of stability may be 20 or 30 days at ethylene oxide production rates of about 2 mole percent.

The amount of cobalt component is generally sufficient to provide an increase in efficiency stability under CONDITIONS of at least about 0.5, preferably at least about 1, efficiency percentage point after 50 days of operation. Most desirably, oxygen process conditions are used. In determining the enhancement in efficiency stability, the process and catalyst should be under steady state conditions. In some instances, the catalyst activates over a period of time, even as much as a week or more, before the catalyst reaches peak initial activity. The reason for this period of activation in some catalysts is not known and may be due to chemical and/or physical conditioning of the catalyst. Therefore, the initial activity of a catalyst is usually determined after the catalyst has been on-stream for at least about 24, preferably for at least about 120 to 170, hours.

The optimal amount of the cobalt component may vary with silver content, the amounts and types of other promoters present and the chemical and physical properties of the carrier. However, the cobalt component is often present in an amount of at least about 10, preferably at least about 25, ppmw (parts per million by weight) calculated as the weight of cobalt on the total catalyst. If too much cobalt component is used, the catalyst performance, e.g., efficiency and/or activity and/or stability, may suffer. If too little cobalt component is present, it is also possible that the performance of the catalyst will suffer or the amount present will be insufficient to show the desired catalytic effect. In determining desired amounts of cobalt component, a traverse of cobalt component concentrations in the catalyst composition can be effected with the catalysts being evaluated for performance. In some instances, it may be desirable to vary the amounts of other components, e.g., silver and other promoters, to achieve beneficial combinations of effects and optimal catalyst performances. Usually, the amount of cobalt component falls within the range of about 25 to 1000, preferably, about 50 to 500, ppmw calculated as the weight of cobalt.

The cobalt component can be provided in various forms, e.g., as a covalent compound such as cobalt oxide, as a cation or as an anion. The specific one or more cobalt species that provide enhanced activity and/or efficiency and/or stability are not certain and may be the component added and/or that generated during catalyst preparation or during use as a catalyst. Although the cobalt species that provide the beneficial properties to the catalysts are not known with specificity, suitable results are obtained when the cobalt component is added to the catalyst in the form of a cation, e.g., cobalt nitrate. The cobalt may be in the +2 oxidation state or +3 oxidation state when added.

Cobalt components include, but are not limited to, cobaltous oxide, cobaltic oxide, cobaltous nitrate, cobaltic nitrate, cobaltous nitrite, cobaltic nitrite, cobaltous sulfate, cobaltic sulfate, cobaltous acetate, cobaltic acetate, cobaltous citrate, cobaltic citrate, cobaltous lactate, cobaltic lactate, cobaltous oxalate, cobaltic oxalate, cobaltous chloride, cobaltic chloride, ammonium cobaltate, cesium cobaltate, potassium cobaltate, sodium cobaltate, cobalt (II) complexes, cobalt (III) complexes and the like. Examples of complexing agents useful in forming the cobalt complexes include ethylenediaminetetraacetic acid (EDTA); N,N'-ethylenediaminediacetic acid; N-hydroxyethylethylenediaminetriacetic acid; diethylenetriaminepentaacetic acid; nitrilotriacetic acid; N-hydroxyethyl-iminodiacetic acid; N-dihydroxyethylglycine; etc . . . Mixtures of cobalt-containing compounds may be used.

As with any catalyst for making ethylene oxide which provides optimum performance, a correlation exists among many factors. Factors frequently considered include:

(i) the nature of the support;

(ii) the amount of silver on or in the support;

(iii) the components and amounts thereof in or on the support;

(iv) the impurities or contaminants provided with the silver or other components;

(v) the procedure to make the catalyst; and (vi) the conditions under which the catalyst is used to produce ethylene oxide.

However, in attempting to define any catalyst, there must be a base value from which other factors are determined especially when the factors are variables, each dependent upon the base value for meaning. In the case of this invention, the base value can be the amount of silver or a combination of the amount of silver and the nature of the support. In most cases the latter combination will be the base value. Because at least two values will comprise the base value for catalyst performance, it is apparent that correlations between such combinations and other factors can be quite complex. There is no common thread of logic which integrates all of these combinations and/or factors. To that extent, practice of the invention requires experimental efforts to achieve all or essentially all of the benefits of this invention. without departing from this script, one skilled in the art can readily achieve the optimum performances of the catalysts of this invention. It should be recognized that such script is commonly followed by the artisan in making any commercially-employable ethylene oxide catalyst. The elements of the script are dependent upon the technology employed in making the catalyst.

The concentration of silver in the finished catalyst may vary from about 2 to 45 or more, often about 2 to 40 or more, weight percent, a commercially preferred range being from about 6% to about 35% by weight of silver. Lower silver concentrations are preferred from an economic standpoint. However, the optimum silver concentration for any particular catalyst will be dependent upon economic factors as well as performance characteristics, such as catalyst efficiency, rate of catalyst aging and reaction temperature.

The support or carrier employed in these catalysts in its broadest aspects is selected from the large number of porous refractory catalyst carriers or support materials which are considered relatively inert in the presence of the ethylene epoxidation feeds, products and reaction conditions. Many such materials are known to persons skilled in the art and may be of natural or synthetic origin and preferably are of a macroporous structure.

The chemical composition of the carrier is not narrowly critical. Carriers may be composed, for example, of alpha-alumina, silicon carbide, silicon dioxide, zirconia, magnesia and various clays. The preferred carriers are alpha-alumina particles often bonded together by a bonding agent and have a very high purity, i.e., at least 98 wt. % alpha-alumina, any remaining components being silica, alkali metal oxides (e.g., sodium oxide) and trace amounts of other metal-containing and/or non-metal-containing additives or impurities; or they may be of lower purity, e.g., about 80 wt. % alpha-alumina, the balance being a mixture of silicon dioxide, various alkali oxides, alkaline earth oxides, iron oxides, and other metal and non-metal oxides. The carriers are formulated so as to be inert under catalyst preparation and reaction conditions. A wide variety of such carriers are commercially available. Alumina carriers are manufactured by United Catalysts, Inc., Louisville, Ky., and the Norton Company, Akron, Ohio.

In the case of alpha alumina-containing supports, preference is given to those having a specific surface area as measured by the B.E.T. method of from about 0.03 $m^2/g$ to about 10 $m^2/g$, preferably from about 0.05 $m^2/g$ to about 5 $m^2/g$, more preferably from about 0.1 $m^2/g$ to about 3 $m^2/g$, and a water pore volume as measured by conventional water absorption techniques of from about 0.1 to about 0.85 cc/g by volume. The B.E.T. method for determining specific surface area is described in detail in Brunauer, S., Emmet, P. and Teller, E. *J. Am. Chem. Soc.,* 60, 309–16 (1938).

Certain types of alpha alumina-containing supports are particularly preferred. These alpha alumina supports have relatively uniform pore diameters and are more fully characterized by having (1) B.E.T. specific surface areas of from about 0.1 $m^2/g$ to about 3.0 $m^2/g$, preferably about 0.1 $m^2/g$ to about 2.0 $m^2/g$ and (2) water pore volumes of from about 0.10 cc/g to about 0.85 cc/g, preferably from about 0.25 cc/g to about 0.75 cc/g. Median pore diameters for the above-described carriers range from about 0.01 to 100 microns, a more preferred range being from about 0.5 to 50 microns. The carriers may have monomodal, bimodal or multimodal pore distributions. Typical properties of some supports found in the literature are shown in Table I.

TABLE I

|  | Carrier | | | | | |
|---|---|---|---|---|---|---|
|  | A | B | C | D | E | F |
| B.E.T. Surface Area $m^2/g^{(a)}$ | 0.21 | 0.42 | 0.42 | 0.48 | 0.57 | 2.06 |
| Water Pore Volume, cc/g | 0.26 | 0.36 | 0.41 | 0.49 | 0.44 | 0.65 |
| Crush Strength, FPCS, lbs[b] | 100% 20 lbs | 97% 15 | Avg. 21 Range 15–30 | 90% 14 | 90% 15 | No Data |
| Total Pore Volume, Hg, cc/g[c] | 0.26 | 0.42 | 0.42 | 0.46 | 0.42 | 0.65 |
| Average Pore Diameter, Hg, Angstroms[c] | 620 | 560 | 640 | 550 | 770 | 1000 |

TABLE I-continued

|  | Carrier | | | | | |
|---|---|---|---|---|---|---|
|  | A | B | C | D | E | F |
| Median Pore Diameter. Hg, microns[c,e] | 3.7 | 2.7 | 3.4 | 3.4 | 2.4 | 2.5 |
| Percent Pore Volume in Pores Greater than 350 Angstroms[c] | 90.0% | 88.5% | 89.5% | 89.1% | 91.5% | 94.1% |
| Percent Pore Volume in Pores Greater than 1 Micron[c] | 87.0% | 82.5% | 83.4% | 82.3% | 83.5% | 61.0% |
| % Wt. Alpha Alumina | 99.5 | 90 | 98.5 | 98.5 | 98 | 70–75 |
| Water Leachable Na, ppmw | 12 | 53 | 21 | 24 | 18 | No Data |
| Acid-Leachable Na, ppmw | 40 | 96 | 87 | 51 | 45 | No Data |
| Water-Leachable K, ppmw | 5 | 22 | 21 | 22 | 10 | No Data |
| Acid-Leachable Fe, ppmw | 2 | 5 | No Data | 1 | 5 | No Data |
| % Wt. $SiO_2$ |  | .5 | 2 | 1.5 | 15 | 2 | 25–30 |

[a]Method of Brunauer, Emmet and Teller, loc. cit.
[b]Flat Plate Crush Strength, single pellet.
[c]Determined by mercury intrusion to 55,000 psia using Micrometrics Autopore 9200 or 9210 (130° Contact angle, 0.473 N/m surface tension of Hg).
[e]Median pore diameter represents the pore diameter wherein 50% of the total pore volume is found in pores having less than (or greater than) the median pore diameter.

Regardless of the character of the support or carrier used, it is preferably shaped into particles, chunks, pieces, pellets, rings, spheres, wagon wheels, cross-partitioned hollow cylinders (or rings), and the like of a size suitable for employment in fixed bed reactors. Conventional commercial fixed bed ethylene oxide reactors are typically in the form of a plurality of parallel elongated tubes (in a suitable shell) approximately 0.7 to 2.7 inches O.D. and 0.5 to 2.5 inches I.D. and 15–45 feet long filled with catalyst. In such reactors, it is desirable to employ a support formed into a rounded shape, such as, for example, spheres, pellets, rings, cross-partitioned rings, tablets and the like, having diameters from about 0.1 inch to about 0.8 inch.

As with any supported catalyst, the optimal performance will depend upon optimizing the carrier in terms of its chemical composition (including impurities), surface area, porosity and pore volume. However, the enhancement in performance provided by this invention may be most pronounced when using less than optimized carriers. Thus, in demonstrating the invention in the examples, a variety of carriers are used.

The catalysts of this invention contain, in addition to the cobalt component, at least one other promoter or modifier to enhance the performance of the catalyst, e.g., to enhance efficiency and/or reduce the burning of ethylene oxide and/or affect activity. These promoters or modifiers are generally provided as chemical compounds.

For the sake of ease of understanding, the promoters will be referred to in terms of cation promoters, e.g., alkali and alkaline earth metals, and anion promoters. Compounds such as alkali metal oxide or $MoO_3$, while not being ionic, may convert to ionic compounds, e.g., during catalyst preparation or in use. Whether or not such a conversion occurs, they will be referred to herein in terms of cation and anion species, e.g., alkali metal or molybdate.

Frequently, the catalyst contains alkali metal and/or alkaline earth metal as cationic promoter. Exemplary of the alkali metal and/or alkaline earth metals are lithium, sodium, potassium, rubidium, cesium, beryllium, magnesium, calcium, strontium and barium. Other cationic promoters include Group 3b metal ions including scandium, yttrium, lanthanum and the lanthanide series metals. In some instances, the promoter comprises a mixture of cations, e.g., cesium and at least one other alkali metal, to obtain a synergistic efficiency enhancement as described in British Patent No. 2,043,481 discussed above. The cation promoter may, of course, provide the counter ion to a cobaltate anion component. Cesium salts alone or in combination with other salts are often used.

In many instances, the catalyst preferably comprises salt (s) of at least one oxyanion of an element (other than oxygen) having an atomic number of 5 to 83 and being from groups 3b through 7b, inclusive, and groups 3a through 7a, inclusive, of the Periodic Table. In some instances, it has been found beneficial to add more anion than is required to associate with the total alkali metal and alkaline earth metal being provided to the catalyst. The reason why such additional anion is beneficial in these situations is not known. The additional anion may be added in the form of an acid, an ammonium salt, an amine salt, etc., or a portion of the alkali metal and/or alkaline earth metal may be added as an acid salt, e.g., cesium hydrogen sulfate.

The concentration of the salt(s) (including any other alkali metal and alkaline earth metal salts) in the finished catalyst is not narrowly critical and may vary over a wide range. The optimum salt concentration for a particular catalyst will be dependent upon performance characteristics, such as, catalyst efficiency, rate of catalyst aging and reaction temperature.

The concentration of salt (based on the weight of the cation, e.g., cesium) in the finished catalyst may vary from about 0.0005 to 1.0 weight percent, preferably from about 0.005 to 0.5 weight percent. The preferred amount of cation promoter deposited on or present on the surface of the carrier or catalyst generally lies between about 10 and about 4000, preferably about 15 and about 3000 and more preferably between about 20 and about 2500 ppm by weight of cation calculated on the total carrier material. Amounts between about 50 and about 2000 ppm are frequently most preferable. When cesium is used in mixture with other cations, the ratio of cesium salt to any other alkali metal and alkaline earth metal salt(s), if used, to achieve desired performance is not narrowly critical and may vary over a wide range. The ratio of cesium salt to the other salt(s) may vary from about 0.0001:1 to 10,000:1, preferably from about 0.001:1 to 1,000:1. Preferably, cesium comprises at least about 10, more preferably, about 20 to 100, percent (weight) of the total added alkali metal and alkaline earth metal in the finished catalyst.

In some preferred embodiments of this invention especially when using other than a redox pair catalyst, the amount of leachable potassium cation as determined by leaching in a mineral acid, particularly nitric acid in a concentration of about 10 percent by volume at a temperature of about 90° C. for about 1 hour followed by washing with distilled water, is less than about 50, preferably less than about 25, e.g., 0 to about 25, ppmw based on the weight of the catalyst. In some instances, the low level of leachable potassium appears, in combination with the cobalt component, to enhance or to permit the cobalt component to achieve greater enhancement of the activity and/or stability of the catalyst. Also, in many instances, preferred embodiments of the catalysts of this invention contain less than about 100, e.g., less than about 50, ppmw of leachable sodium cation as determined by the above procedure.

The types of anion promoters or modifiers suitable for use in the catalysts of this invention comprise, by way of example only, oxyanions such a sulfate, $SO_4^{-2}$, phosphates, e.g., $PO_4^{-3}$, titanates, e.g., $TiO_3^{-2}$, manganates, e.g., $MnO_2^{-}$, tantalates, e.g., $Ta_2O_6^{-2}$, molybdates, e.g., $MoO_4^{-2}$, vanadates, e.g., $V_2O_4^{-2}$, chromates, e.g., $CrO_4^{-2}$, zirconates, e.g., $ZrO_3^{-2}$, polyphosphates, nitrates, chlorates, bromates, borates, silicates, carbonates, tungstates, thiosulfates, cerates and the like. Halide ions may also be present as anions and include fluoride, chloride, bromide and iodide.

It is well recognized that many anions have complex chemistries and may exist in one or more forms, e.g., orthovanadate and metavanadate; and the various molybdate oxyanions such as $MoO_4^{-2}$, $Mo_7O_{24}^{-6}$ and $Mo_2O_7^{-2}$. The oxyanions may also include mixed metal-containing oxyanions including polyoxyanion structures. For instance, manganese and molybdenum can form a mixed metal oxyanion. Similarly, other metals, whether provided in anionic, cationic, elemental or covalent form may enter into anionic structures.

While an oxyanion, or a precursor to an oxyanion, may be used in solutions impregnating a carrier, it is possible that during the conditions of preparation of the catalyst and/or during use, the particular oxyanion or precursor initially present may be converted to another form. Indeed, the element may be converted to a cationic or covalent form. Preferably, the element is associated with oxygen, i.e., is an oxyanion, a covalent oxide or has an oxygen-containing anion. In many instances, analytical techniques may not be sufficient to precisely identify the species present. The invention is not intended to be limited by the exact species that may ultimately exist on the catalyst during use but rather reference herein to oxyanions is intended to provide guidance to understanding and practicing the invention.

Anion promoters include, but are not limited to, the sulfates and oxyanions of rhenium, molybdenum, tungsten and/or chromium. Examples of anions of sulfur that can be suitably applied include sulfate, sulfite, bisulfite, bisulfate, sulfonate, persulfate, thiosulfate, dithionate, dithionite, halosulfate, e.g., fluorosulfate, etc. Preferred compounds to be applied are ammonium sulfate and the alkali metal sulfates. Examples of anions of molybdenum, tungsten and chromium that can be suitably applied include molybdate, dimolybdate, paramolybdate, other iso- and heteropolymolybdates, etc.; tungstate, paratungstate, metatungstate, other iso- and hetero-polytungstates, etc.; and chromate, dichromate, chromite, halochromate, etc. Preferred are sulfates, molybdates, tungstates and chromates.

When the catalyst comprises rhenium, the rhenium component can be provided in various forms, e.g., as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, alkaline earth metal perrhenates, silver perrhenates, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, i.e., $ReO_4$. Similar chemistries can be exhibited by other metals such as molybdenum and tungsten.

The amount of anion promoter may vary widely, e.g., from about 0.0005 to 2 weight percent, preferably from about 0.001 to 0.5 weight percent based on the total weight of the catalyst. When used, the rhenium component is often provided in an amount of at least about 1, say, at least about 5, e.g., about 10 to 2000, often between about 20 and 1000, ppmw calculated as the weight of rhenium based on the total weight of the catalyst.

Another class of promoters includes manganese components. In many instances, manganese components can enhance the activity and/or stability of catalysts. The manganese species that provides the enhanced activity and/or stability is not certain and may be the component added or that generated either during catalyst preparation or during use as a catalyst. Manganese components include, but are not limited to, manganese acetate, manganese ammonium sulfate, manganese citrate, manganese dithionate, manganese oxalate, manganous nitrate, manganous sulfate, and manganate anion, e.g., permanganate anion, manganate anion, manganese complexes, e.g., with manganese in the +2 or +3 oxidation state and complexed with a complexing agent, such as a complexing agent selected from those set forth elsewhere herein, and the like. When used, the manganese component is often provided in an amount of at least about 1, say, at least about 5, e.g., about 10 to 2000, or about 20 to 1000, ppmw calculated as the weight of manganese based on the total weight of the catalyst.

The catalysts of this invention may be of the type comprising at least one efficiency-enhancing salt of a member of a redox-half reaction pair which are intended to be employed in epoxidation processes in which at least one efficiency-enhancing gaseous member of a redox-half reaction pair is present (described hereinbelow). The term "redox-half reaction" is defined herein to mean half-reactions like those found in equations presented in tables of standard reduction or oxidation potentials, also known as standard or single electrode potentials, of the type found in, for instance, "Handbook of Chemistry", N. A. Lange, Editor, McGraw-Hill Book Company, Inc., pages 1213–1218 (1961) or "CRC Handbook of Chemistry and Physics", 65th Edition, CRC Press, Inc., Boca Raton, Fla., pages D155–162 (1984). The term "redox-half reaction pair" refers to the pairs of atoms, molecules or ions or mixtures thereof which undergo oxidation or reduction in such half-reaction equations. Such terms as redox-half reaction pairs are used herein to include those members of the class of substances which provide the desired performance enhancement, rather than a mechanism of the chemistry occurring. Preferably, such compounds, when associated with the catalyst as salts of members of a half reaction pair, are salts in which the anions are oxyanions, preferably an oxyanion of a polyvalent atom; that is, the atom of the anion to which oxygen is bonded is capable of existing, when bonded to a dissimilar atom, in different valence states. Potassium is the preferred cation, although sodium, rubidium and cesium may also be operable, and the preferred anions are nitrate, nitrite and other anions capable of undergoing displacement or other chemical reaction and forming nitrate anions under epoxidation conditions. Preferred salts include $KNO_3$ and $KNO_2$, with $KNO_3$ being most preferred.

The salt of a member of a redox-half reaction pair is added in an amount sufficient to enhance the efficiency of the epoxidation reaction. The precise amount will vary depending upon such variables as the gaseous efficiency-enhancing member of a redox-half reaction used and concentration thereof, the concentration of other components in the gas phase, the amount of silver contained in the catalyst, the surface area of the support, the process conditions, e.g., space velocity and temperature, and morphology of support. Generally, however, a suitable range of concentration of the added efficiency-enhancing salt, calculated as cation, is about 0.01 to about 5 percent, preferably about 0.02 to about 3 percent, by weight, based on the total weight of the catalyst. Most preferably the salt is added in an amount of about 0.03 to about 2 weight percent.

In any event, each promoter, such as each metal-containing promoter, e.g., whether cationic, anionic or nonionic, is provided in a promoting amount. As used herein the term "promoting amount" of a certain component of a catalyst refers to an amount of that component that works effectively to provide an improvement or enhancement in one or more of the catalytic properties of that catalyst when compared to a catalyst not containing said component. Examples of catalytic properties include, inter alia, operability (resistance to run-away), selectivity, activity, conversion, stability and yield. It is understood by one skilled. in the art that one or more of the individual catalytic properties may be enhanced by the "promoting amount" while other catalytic properties may or may not be enhanced or may even be diminished. Indeed, the promoter may enhance efficiency but decrease activity of the catalyst as determined under Standard Ethylene Oxide Process Conditions. It is further understood that different catalytic properties may be enhanced at different operating conditions. For example, a catalyst having enhanced selectivity at one set of operating conditions may be operated at a different set of conditions wherein the improvement shows up in the activity rather than the selectivity and an operator of an ethylene oxide plant will intentionally change the operating conditions in order to take advantage of certain catalytic properties even at the expense of other catalytic properties in order to maximize profits by taking into account feedstock costs, energy costs, by-product removal costs and the like.

The promoting effect provided by the promoters can be affected by a number of variables such as for example, reaction conditions, catalyst preparative techniques, surface area and pore structure and surface chemical properties of the support, the silver and co-promoter content of the catalyst, and the presence of other cations and anions present on the catalyst. The presence of other activators, stabilizers, promoters, enhancers or other catalyst improvers can also affect the promoting effects.

A variety of procedures may be employed for preparing catalysts in accordance with the present invention. The preferred procedure comprises: (1) impregnating a porous catalyst carrier with a solution comprising a solvent or solubilizing agent, silver complex and any promoter or promoters in amounts sufficient to deposit the desired weight of silver and the aforementioned promoter or promoters upon the carrier, and (2) thereafter treating the impregnated support to convert the silver salt to silver metal and effect deposition of silver and the promoter or promoters onto the exterior and interior surfaces of the support. For sake of repeatability, in the use and reuse of impregnating solutions the carrier should preferably not contain undue amounts of ions which are soluble in the impregnating solution and/or exchangeable with the promoter or promoters supplied to the catalyst, either in the preparation or use of the catalyst, so as to upset the amount of promoter which provides the desired catalyst enhancement. If the carrier contains such ions, the ions should generally be removed by standard chemical techniques such as leaching. Silver and promoter depositions are generally accomplished by heating the carrier at elevated temperatures to evaporate the remaining liquid within the support and effect deposition of the silver and promoter or promoters onto the interior and exterior carrier surfaces. Impregnation of the carrier is the preferred technique for silver deposition because it utilizes silver more efficiently than coating procedures, the latter being generally unable to effect substantial silver deposition onto the interior surface of the carrier. In addition, coated catalysts are more susceptible to silver loss by mechanical abrasion.

The sequence of impregnating or depositing the surfaces of the carrier with silver and promoters is optional. Thus, impregnation and deposition of silver and salts may be effected coincidentally or sequentially, i.e., the promoters may be deposited prior to, during, or subsequent to silver addition to the carrier. The promoters may be deposited together or sequentially. For example, one or more of the salts may be deposited first followed by the coincidental or sequential deposition of silver and additional or other salts. In instances in which the silver component in the silver impregnation solution may interfere with the compound providing the promoter, or, alternatively, the compound providing the promoter may interfere with the silver component in the impregnation solution, it is frequently desirable to use a sequential deposition process in which the silver is deposited and calcined and then the promoter compound is impregnated onto the support.

Impregnation of the catalyst carrier is effected using one or more solutions containing silver and promoters in accordance with well-known procedures for coincidental or sequential depositions. For coincidental deposition, following impregnation the impregnated carrier is heat or chemically treated to reduce the silver compound to silver metal and deposit the salts onto the catalyst surfaces.

For sequential deposition, the carrier is initially impregnated with silver or promoter (depending upon the sequence employed) and then heat or chemically treated as described above. This is followed by a second impregnation step and a corresponding heat or chemical treatment to produce the finished catalyst containing silver and promoters.

In one useful embodiment, the silver-containing carrier is subsequently impregnated using a solution containing a metal-containing promoter other than alkali metals or alkaline earth metals, the solution being chosen so that the metal-containing promoter has an increased affinity to the silver-containing carrier relative to its affinity to the carrier without silver and/or is associated with, preferably adsorbed on and more preferably deposited on, the silver-containing carrier at an increased rate relative to the rate at which the promoter would be associated with the carrier without silver. This method facilitates catalyst preparation and produces catalysts which are effective for alkene epoxidation. This method is more fully described in commonly assigned U.S. patent application Ser. No. 07/596,228, filed Oct. 12, 1990 now U.S. Pat. No. 5,112,795, which is incorporated in its entirety herein by reference.

In making the catalysts of this invention, some promoters such as some alkali and alkaline earth metal salts have such high melting temperatures that when deposited on the support with silver compound, and subjected to heating to convert the silver compound to silver metal, the salts may remain essentially unchanged. Of course, it is realized that alkali metal and alkaline earth metal salts having an unstable oxidation state will change to a stable oxidation state or states, e.g., sulfites to sulfates. When, for instance, the alkali metal or alkaline earth metal is deposited as the hydroxide or carbonate, it may be transformed in the presence of amines, which may be used in the impregnation of the catalyst, to a different salt form (i.e., nitrate) during the heating (roasting) step depending on the roast conditions.

The silver solution used to impregnate the carrier is comprised of a silver compound in a solvent or complexing/solubilizing agent such as the silver solutions disclosed in the art. The particular silver compound employed may be chosen, for example, from among silver complexes, nitrate, silver oxide or silver carboxylates, such as silver acetate, oxalate, citrate, phthalate, lactate, propionate, butyrate and higher fatty acid salts. Desirably, silver oxide complexed with amines is the preferred form of silver in the practice of the invention.

A wide variety of solvents or complexing/solubilizing agents may be employed to solubilize silver to the desired concentration in the impregnating medium. Among those disclosed in the art as being suitable for this purpose are lactic acid (U.S. Pat. No. 2,477,436 to Aries; and U.S. Pat. No. 3,501,417 to DeMaio); ammonia (U.S. Pat. No. 2,463,228 to West, et al.); alcohols, such as ethylene glycol (U.S. Pat. No. 2,825,701 to Endler, et al.,; and U.S. Pat. No. 3,563,914 to Wattimina); and amines and aqueous mixtures of amines (U.S. Pat. No. 2,459,896 to Schwarz; U.S. Pat. No. 3,563,914 to Wattimina; U.S. Pat. No. 3,215,750 to Benisi; U.S. Pat. No. 3,702,259 to Nielsen; and U.S. Pat. Nos. 4,097,414, 4,374,260 and 4,321,206 to Cavitt).

The metal-containing promoter or promoters themselves may be present as complexes in the impregnating solution, in particular in such a solution which also contains silver, prior to being associated with the carrier. Such complexes may conveniently be derived by including one or more complexing agents effective to form a complex with at least one metal species, e.g., metal-containing promoter precursor, in the impregnating solution, or solution precursor (e.g., a liquid medium containing undissolved metal-containing promoter precursor) in an amount effective to enhance the solubility and/or solubility stability of the metal-containing promoter in the solution or solution precursor. The enhancement in solubility and/or solubility stability is determined by comparing similar impregnating solutions or solution precursors in which the metal-containing promoter is complexed and in which the metal-containing promoter is not complexed with the complexing agent and/or with and without the complexing agent. The term "solubility stability" is a measure of the ability of a metal-containing promoter to remain in solution over time, the longer the time the more solubility stable the metal-containing promoter is.

The complexing agent or agents useful to form the metal-containing promoter complexes thereof may be chosen, e.g., from among conventional and well known complexing agents, to provide the desired solubility and/or solubility stability. The selection of the particular complexing agent or agents to be employed is dependent on many factors, such as, the metal-containing promoter to be employed, the composition of the impregnation solution or solution precursor, the conditions at which the impregnation solution or solution precursor is to be held prior to being used to impregnate the carrier, etc. Examples of complexing agents which may be useful include ethylenediaminetetraacetic acid (EDTA); N,N'-ethylenediaminediacetic acid; N-hydroxyethylethylenediaminetriacetic acid; diethylenetriaminepentaacetic acid; nitrilotriacetic acid; N-hydroxyethyl-iminodiacetic acid; N-dihydroxyethylglycine; etc . . .

The amount of complexing agent employed varies widely, for example, depending on the specific complexing agent and on the specific metal species to be complexed, and on the amount of metal to be complexed. Preferably, the amount of complexing agent is at least about 50%, more preferably at least about 100%, of that needed to form complexes with the metal species to be complexed in the impregnating solution or solution precursor. Excesses of complexing agent over that needed to form the desired complexes may be employed, for example, so that the complexes can be maintained over a relatively long period of time. For example, the complexing agent may be included in an amount of at least about 150% or at least about 200% or at least about 400% or more of that needed to form the desired complexes. The amount of the complexing agent employed, e.g., in the impregnating solution or solution precursor, includes both the complexing agent which is complexed with the metal species and the additional or excess complexing agent, if any, which is present in the impregnating solution or solution precursor and is not so complexed.

A particularly preferred process for making high silver content catalysts involves two or more sequential impregnations of silver, with or without promoters, each of which impregnations may be followed by roasting or other procedure to render the silver insoluble. Advantageously, the carrier has a high pore volume and surface area when using high silver loadings.

Following impregnation of the catalyst carrier with silver and/or promoter or promoters, the impregnated carrier particles are separated from any remaining non-absorbed solution. This is conveniently accomplished by draining the excess impregnating medium or, alternatively, by using separation techniques, such as filtration or centrifugation. The impregnated carrier is then generally heat treated (e.g., roasted) to effect decomposition and reduction of the silver metal compound (complexes in most cases) to metallic silver and/or the deposition of the promoter or promoters. Such roasting may be carried out at a temperature of from about 100° C. to 900° C., preferably from 200° C. to 700° C., for a period of time sufficient to convert substantially all of the silver salt to silver metal and/or to effect deposition of substantially all of the promoter or promoters. In general, the higher the temperature, the shorter the required time period. For example, at a temperature of from about 400° C. to 900° C., silver reduction may be accomplished in about 1 to 5 minutes. Although a wide range of heating periods have been suggested in the art to thermally treat the impregnated support, (e.g., U.S. Pat. No. 3,563,914 suggests heating for less than 300 seconds to dry, but not roast to reduce, the catalyst; U.S. Pat. No. 3,702,259 discloses heating from 2 to 8 hours at a temperature of from 100° C. to 375° C. to reduce the silver salt in the catalyst; and U.S. Pat. No. 3,962,136 suggests ½ to 8 hours for the same temperature range), it is only important that the time be correlated with temperature such that substantially complete reduction of the silver salt to metal and/or substantially complete deposition of the promoter or promoters are accomplished. A continuous or step-wise heating program is desirably used for this purpose. Continuous roasting of the catalyst for a short period of time, such as for not longer than ½ hour is preferred and can be effectively done in making the catalysts of this invention.

Heat treatment is preferably carried out in air, but a nitrogen or carbon dioxide atmosphere may also be employed. The equipment used for such heat treatment may use a static or flowing atmosphere of such gases to effect reduction, but a flowing atmosphere is much preferred.

An important consideration in making the catalyst of this invention is to avoid the use of strongly acidic or basic solutions which can attack the support and deposit impurities which can adversely affect the performance of the catalyst. The preferred impregnation procedure of U.K. Patent 2,043,481 coupled with the high roasting temperature, short residence time procedure which the patent also described is especially beneficial in minimizing such catalyst contamination. However, the use of the salts of this invention coupled with the high purity supports allows one to use lower temperatures though short residence times are preferred.

The particle size of silver metal deposited upon the carrier is asserted by a portion of the prior art to be a function of the catalyst preparation procedure employed. This may seem to be the case because of the limited ability of the art to effectively view the surface of the catalyst. Thus the space between the silver particles seen on the carrier has not been characterized sufficiently to say whether such particles of silver represent all the silver on the carrier. However, the particular choice of solvent and/or complexing agent, silver compound, heat treatment conditions and catalyst carrier may affect, to varying degrees, the range of the size of the resulting silver particles seen on the carrier. For carriers of general interest for the production of ethylene oxide, a distribution of silver particle sizes in the range of 0.005 to 2.0 microns is typically obtained. However, the role of particle size of the silver catalyst upon the effectiveness of the catalyst in making ethylene oxide is not clearly understood. In view of the fact that the silver particles are known to migrate on the surface of the catalyst when used in the catalytic reaction resulting in a marked change in their size and shape while the catalyst is still highly effective suggests that the silver particle size viewed on the support may not be a significant factor in catalytic performance.

The silver catalysts of the invention are particularly suitable for use in the production of ethylene oxide by the vapor phase oxidation of ethylene with molecular oxygen. The reaction conditions for carrying out the oxidation reaction are well-known and extensively described in the prior art. This applies to reaction conditions, such as temperature, pressure, residence time, concentration of reactants, gas phase diluents (e.g., nitrogen, methane and $CO_2$), gas phase inhibitors (e.g., ethylene chloride and ethylene dichloride), and the like.

The gases fed to the reactor may contain modifiers or inhibitors or additives such as disclosed by Law, et al., in U.S. Pat. Nos. 2,279,469 and 2,279,470, such as nitrogen oxides and nitrogen oxides generating compounds. See also, European Patent No. 3642 which describes catalysts comprising at least one efficiency-enhancing salt of a redox-half reaction pair in conjunction with at least one gaseous efficiency-enhancing member of a redox-half reaction pair.

The terms "gaseous member of a redox-half reaction pair", "gaseous efficiency-enhancing member of a redox-half reaction pair", or like terms referred to herein have a meaning similar to that for the "salt of a member of a redox-half reaction pair" or like terms, defined above. That is, these terms refer to members of half-reactions, represented in standard or single electrode potential tables in standard reference texts or handbooks which are in a gaseous state and are substances which, in the reaction equations represented in the texts, are either oxidized or reduced. The preferred gaseous efficiency-enhancing materials are compounds containing an element capable of existing in more than two valence states, preferably nitrogen and another element which is, preferably, oxygen. Examples of preferred gaseous efficiency-enhancing members of redox-half reaction pairs include at least one of NO, $NO_2$, $N_2O_3$, $N_2O_4$, $N_2O_5$ or any gaseous substance capable of forming one of the aforementioned gases, particularly NO and $NO_2$, under epoxidation conditions, and mixtures thereof with one or more of $PH_3$, CO, $SO_3$, $SO_2$, $P_2O_5$, and $P_2O_3$. NO is often preferred as the gaseous efficiency-enhancing compound.

Although in some cases it is preferred to employ members of the same half-reaction pair in the reaction system, i.e., both the efficiency-enhancing salt member associated with the catalyst and the gaseous member in the feedstream, as, for example, with a preferred combination of potassium nitrate and nitric oxide, this is not necessary in all cases to achieve satisfactory results. Other combinations, such as $KNO_3/N_2O_3$, $KNO_3/NO_2$, $KNO_3/N_2O_4$, $KNO_3/SO_2$, $KNO_2/$NO, $KNO_2/NO_2$ and $KNO_3$/a mixture of $SO_2$ and NO, may also be employed in the same system. In some instances, the salt and gaseous members may be found in different half-reactions which represent the first and last reactions in a series of half-reaction equations of an overall reaction.

The gaseous efficiency-enhancing member of a redox-half reaction pair is also present in an amount sufficient to enhance the performance, such as the activity of the catalyst, and, particularly, the efficiency of the epoxidation reaction. The precise amount is determined, in part, by the particular efficiency-enhancing salt of a member of a redox-half reaction pair used and the concentration thereof, the particular alkene undergoing oxidation, and by other factors noted above which influence the amount of efficiency-enhancing salt of a member of a redox-half reaction pair. Typically a suitable concentration of the gaseous member of a redox-half reaction pair for epoxidation of most alkenes, including propylene, is about 0.1 to about 2,000 ppm, by volume, of the gaseous feedstream when $N_2$ is used as ballast. When a preferred gaseous member of a redox-half reaction pair, such as NO, is used in the epoxidation of propylene, the preferred concentration is about 2,000 ppm, by volume, with an $N_2$ ballast. However, when ethylene is being oxidized, a suitable concentration is from about 0.1 to about 100 ppm, by volume, of the gaseous feedstream components. Preferably, the gaseous efficiency-enhancing member of a redox-half reaction pair is present in an amount of about 1 to about 80 ppm when about 3 percent, by volume, $CO_2$ is present in the reaction mixture. When nitric oxide is employed as the gaseous efficiency-enhancing compound in an ethylene epoxidation system, it is present in an amount of about 0.1 to about 60 ppm, preferably about 1 to about 40 ppm, when $CO_2$ is present in the reaction mixture, e.g., in amounts up to about 3 volume percent.

The desirability of recycling unreacted feed, or employing a single-pass system, or using successive reactions to increase ethylene conversion by employing reactors in series arrangement can be readily determined by those skilled in the art. The particular mode of operation selected will usually be dictated by process economics.

Generally, the commercially-practiced processes are carried out by continuously introducing a feed stream containing ethylene and oxygen to a catalyst-containing reactor at a temperature of from about 200° C. to 300° C., and a pressure which may vary from about five atmospheres to about 30 atmospheres depending upon the mass velocity and productivity desired. Residence times in large-scale reactors are generally on the order of about 0.1–5 seconds. Oxygen may be supplied to the reaction in an oxygen-containing stream, such as air or as commercial oxygen. The resulting ethylene oxide is separated and recovered from the reaction products using conventional methods. However, for this invention, the ethylene oxide process envisions the normal gas recycle encompassing carbon dioxide recycle in the normal concentrations, e.g., about 0.5 to 6 volume percent.

The present cobalt-containing catalyst may be used selectively to enhance the effectiveness of an alkene epoxidation process, as described herein. For example, the present cobalt-containing catalyst may be effective to increase or enhance the rate of start-up of the alkene epoxidation process. In addition, the catalyst may provide increased catalyst effectiveness stability along the length of a fixed bed of catalyst relative to a similar catalyst which includes no cobalt component, e.g., at CONDITIONS. These features of the present cobalt-containing catalysts are more fully described in commonly assigned U.S. patent application Ser. No. 07/596,242 filed Oct. 12, 1990, now abandoned, which application is incorporated herein in its entirety by reference.

The specific STANDARD ETHYLENE OXIDE PROCESS CONDITIONS are used in the examples below unless indicated otherwise. In commercial processes, typical operating conditions can vary and the amounts of the ingredients employed can be adjusted to achieve the best efficiencies. In particular the amounts of ethane, carbon dioxide and organic chloride can be varied to optimize efficiency for the manufacture of ethylene oxide. Ethane is an impurity contained in varying amounts in ethylene raw material. Ethane can also be added to a commercial reactor to provide better control of the chloride's inhibitor action. Typically, the amount of ethane used in commercial processes can vary from about 0.001 to about 5 mole percent for achieving optimization under both air process conditions and oxygen process conditions. As the concentration of ethane increases in the reactor, the effective surface chloride concentration on the catalyst is believed to be decreased thereby decreasing the ability of chloride to promote/inhibit reactions that increase efficiency for the manufacture of ethylene oxide. The amount of chloride, e.g., ethyl chloride or ethylene dichloride, can be varied to provide the needed promoter/inhibitor action commensurate with the ethane levels encountered in a particular process and the type of promoters or modifiers used in the catalyst. The amount of organic chloride used in commercial processes can typically vary from about 1.0 ppm to about 100 ppm for achieving optimization under both air process conditions and oxygen process conditions. Carbon dioxide is generally considered an inhibitor, and the inhibitor effect of carbon dioxide on process efficiency may be variable with its concentration. With different types of promoters or modifiers used in preparation of the catalysts of this invention, different concentrations of carbon dioxide may be more desirable in certain commercial processes. Typically, the amount of carbon dioxide used in commercial processes can vary from about 2 to about 15 mole percent for achieving optimization under both air process conditions and oxygen process conditions. The amount of carbon dioxide is dependent on the size and type of carbon dioxide scrubbing system employed. The optimization of the amounts of ethane, carbon dioxide and organic chloride provides catalysts which are especially suitable for obtaining desired efficiencies in commercial ethylene oxide manufacture. Especially in the epoxidation processes using at least one gaseous efficiency-enhancing member of a redox-half reaction pair in conjunction with at least one salt of a member of a redox-half reaction pair on the catalyst, the concentration of carbon dioxide is preferably maintained below about 1.5, e.g., below about 1.0 or even about 0.5, volume percent.

Catalysts which have been subjected to process conditions for ethylene oxide manufacture such as STANDARD ETHYLENE OXIDE PROCESS CONDITIONS are considered an important aspect of this invention.

EXAMPLES

The following examples are by way of illustration only and are not to be construed as limiting the scope of the invention described herein.

Silver and promoter concentrations for all catalysts described in the specification are calculated values as described above.

Unless otherwise specified, carriers are nominally ring shaped having dimensions of about ⅛×5/16×5/16 inch or about ⅛×¼×¼ inch.

The following carriers are employed in one or more of the present examples.

Carrier "N"

Chemical Composition of Carrier "N"

alpha-Alumina at least about 98 wt. %
Acid Leachable Impurities
Leachate contained 378 ppm sodium and 330 ppm potassium.

| Physical Properties of Carrier "N" | |
|---|---|
| Surface Area(1) | 1.166 m$^2$/g |
| Pore Volume (2) | 0.697 cc/g |
| Packing Density (3) | 34.2 lbs/ft$^3$ |
| Median Pore Diameter (4) | 15 microns |
| Apparent Porosity (%) | 72 |
| % Water Absorption | 65.4 |
| Bulk density | 1.1 g/cc |

Carrier S

Carrier S is an alpha-alumina carrier prepared by calcining a boehmite-ammonium bifluoride mixture containing 3 weight percent of ammonium bifluoride first at about 600° C. and calcining again at about 1025° C. The chemical and physical properties of the carrier are given below:

| Chemical Composition of Carrier S | |
|---|---|
| alpha-Alumina | 99 wt % |
| Fluoride | 0.25 wt % |

Water Leachable Impurities 6 ppm aluminum, 9 ppm calcium, 5 ppm magnesium, 1 ppm potassium, 13 ppm sodium, 36 ppm fluoride, 1 ppm sulfate.

| Physical Properties of Carrier S | |
|---|---|
| Surface Area[1] | 1.24 m$^2$/g |
| Pore Volume[2] | 0.77 cc/g |
| Packing Density[3] | 0.50 g/ml |
| Medium Pore Diameter[4] | 1.7 microns |

| Pore Size Distribution, % Total Pore Volume | |
|---|---|
| Pore Size Microns | % Total Pore Volume |
| $P_1$ (<0.1) | 0.5 |
| $P_2$ (0.1–0.5) | 3 |
| $P_3$ (0.5–1.0) | 9.5 |
| $P_4$ (1.0–10) | 81 |
| $P_5$ (10–100) | 2 |
| $P_6$ (>100) | 4 |

CARRIER T

Carrier T is an alpha-alumina carrier prepared by calcining a boehmite-ammonium bifluoride mixture containing 3 weight percent of ammonium bifluoride first at about 600° C. and calcining again at about 1025° C. The chemical and physical properties of the carrier are given below:

| Chemical Composition of Carrier T | |
|---|---|
| alpha-Alumina | 99 wt % |
| Fluoride | 0.25 wt % |

Water Leachable Impurities 8 ppm aluminum, 17 ppm calcium, 8 ppm magnesium, 5 ppm potassium, 6 ppm sodium, 55 ppm fluoride, 1 ppm sulfate.

| Physical Properties of Carrier T | |
|---|---|
| Surface Area(1) | 1.13 m$^2$/g |
| Pore Volume(2) | 0.75 cc/g |
| Packing Density(3) | 0.51 g/ml |
| Medium Pore Diameter(4) | 2.1 microns |

| Pore Size Distribution, % Total Pore Volume | |
|---|---|
| Pore Size Microns | % Total Pore Volume |
| $P_1$ (<0.1) | 0 |
| $P_2$ (0.1–0.5) | 1 |
| $P_3$ (0.5–1.0) | 4.5 |
| $P_4$ (1.0–10) | 90.5 |
| $P_5$ (10–100) | 1.5 |
| $P_6$ (>100) | 2.5 |

Carrier U

Carrier U is Carrier T which had been washed five times with hot deionized water (approximately 70° C.).

Carrier V

Carrier V is an alpha-alumina carrier prepared by calcining a boehmite-ammonium bifluoride mixture containing 3 weight percent ammonium bifluoride first at about 600° C. and again at about 1025° C. The carrier pills are extruded with a cross-partitioned ring cross-sectional geometry and have a nominal length and diameter of about 0.31 inches. By weight, the carrier includes at least 99% alpha-alumina and about 0.25% fluoride. Other chemical and physical properties of this carrier are given below:

| Water-leachable impurities | |
|---|---|
| aluminum | 59 ppm |
| calcium | 4 ppm |
| magnesium | 7 ppm |
| sodium | 16 ppm |
| silicon | 1 ppm |
| zinc | 1 ppm |
| nitrate | 1 ppm |
| phosphate | 1 ppm |
| sulfate | 20 ppm |
| fluoride | 161 ppm |
| Physical properties | |
| surface area (1) | 1.16 m$^2$/g |
| pore volume (2) | 0.76 cc/g |
| packing density (3) | 0.50 g/ml |
| median pore diameter (4) | 2.3 microns |
| Pore size distribution | |
| pore size, microns | % total pore volume |
| <0.1 | 0 |
| 0.1–0.5 | 1 |
| 0.5–1.0 | 5 |
| 1.0–10 | 88 |
| 10–100 | 2 |
| >100 | 4 |

(1) Method of Measurement described in "Adsorption Surface Area and Porosity", S. J. Gregg and K. S. W. Sing, Academic Press (1967), pages 316–321.
(2) Method of Measurement as described in ASTM C20–46.
(3) Calculated value based on conventional measurement of the weight of the carrier in a known volume container.
(4) Method of Measurement described in "Application of Mercury Penetration to Materials Analysis", C. Orr, Jr., Powder Technology, Vol. 3, pp. 117–123 (1970).

The identity and amounts of water leachable components of carriers can be determined by any convenient analytical technique. Generally, the carriers are heated in distilled water at a temperature of about 50° to 95° C., often 90° C., for about 0.5 to 2, e.g., 1 hour. The liquid is then subjected to ion chromatography and Inductively Coupled Plasma Spectroscopy techniques.

Stock Silver Solutions

Some of the silver impregnating solutions used during preparation of the example catalysts presented below are made on a large scale using the following procedure. The indicated amount of ethylenediamine (by weight) is mixed with the initial amount of distilled water. Oxalic acid dihydrate is slowly added such that the exotherm does not cause the temperature of the solution to rise above about 40° C. The indicated amount of silver oxide is added, followed by monoethanolamine. Distilled water is added to bring the solution to the desired final weight.

| Component (parts by weight) | Type A | Type B | Type C |
|---|---|---|---|
| ethylenediamine | 11.43 | 11.47 | 11.43 |
| initial water | 20.00 | 20.00 | 24.00 |
| oxalic acid dihydrate | 11.60 | 11.60 | 11.60 |

-continued

| Component (parts by weight) | Type A | Type B | Type C |
|---|---|---|---|
| silver oxide | 19.82 | 19.82 | 19.82 |
| monoethanolamine | 4.00 | 4.01 | 4.00 |
| add water to final weight of | 71.00 | 71.00 | 75.00 |

Examples 1–3

The preparation technique for the catalysts of Examples 1 (comparative), 2, and 3 is as follows. For the first impregnation, a weighed amount of carrier S is placed in an impregnation vessel. The vessel is evacuated using a mechanical vacuum pump and the designated stock silver solution is added. The solution is allowed to contact the carrier for 30 minutes at atmospheric pressure and is then allowed to drain from the carrier for 15 minutes. The first impregnated carrier is calcined in air on a belt roaster using the following procedure. The first impregnated carrier is spread out in a single layer and transported on a stainless steel belt through a 2 in. by 2 in. square heating zone in 2.5 minutes. Hot air, heated externally by a tubular furnace, is discharged from a port immediately below the belt at about 500° C. at a rate of 66 standard cubic feet per hour per square inch. The roasted carrier is then returned to the impregnation vessel for the second impregnation. The solution for the second impregnation is prepared by adding $KNO_3$ to the designated silver solution while stirring vigorously. The indicated amount of $Co(NO_3)_2 \cdot 6H_2O$, when used, is first dissolved in a small amount of water and then added to the impregnating solution. The second impregnation is promptly carried out and the resulting second impregnated carrier is calcined again, both second impregnating and calcining processes being conducted in the manner described above. For the catalysts of Examples 1–3, specific details of the preparative procedure and the resulting catalysts are given below:

|  | Example 1 (comparative) | Example 2 | Example 3 |
|---|---|---|---|
| carrier type | S | S | S |
| silver solution type | B | C | A |
|  | Wt. parts | Wt. parts | Wt. parts |
| carrier | 61.10 | 60.62 | 61.30 |
| First impregnation: |  |  |  |
| silver solution | 192.5 | 184.7 | 191.1 |
| Second impregnation: |  |  |  |
| silver solution | 190.2 | 190.0 | 186.8 |
| $KNO_3$ | 1.125 | 1.018 | 1.011 |
| $Co(NO_3)_2 \cdot 6H_2O$ | — | 0.201 | 0.387 |
| Catalyst Composition: |  |  |  |
| Wt. % Ag | 35.3 | 33.7 | 35.3 |
| ppmw K | 1405 | 1394 | 1367 |
| ppmw Co | — | 139 | 271 |

The prepared catalysts are evaluated in standard back-mixed autoclaves generally in accordance with the test procedure described previously with regard to the CONDITIONS. Approximately 80 cc of each catalyst is tested at a nominal gas space velocity of 8000 hr$^{-1}$ using the following feed gas composition: 8 volume % oxygen, 30 volume % ethylene, about 5 ppmw ethyl chloride, about 5 ppmw nitric oxide, and the balance nitrogen. The catalysts of Examples 1 and 2 are initially operated at 220° C. and the temperature is raised on successive days to 230, 240, and 255° C. The catalyst for Example 3 is started at 240° C. and raised to 255° C. on the following day. The concentrations of ethyl chloride and nitric oxide are adjusted as necessary to optimize the combination of activity and efficiency. The following performance is observed:

| Example | Day 11 % EO (outlet) | % efficiency | Day 30 % EO (outlet) | % efficiency |
|---|---|---|---|---|
| 1 (comparative) | 2.22 | 85.2 | 1.59 | 85.2 |
| 2 | 2.23 | 86.2 | 2.05 | 86.0 |
| 3 | 2.21 | 85.1 | 2.03 | 85.7 |

These results indicate that the cobalt-containing catalysts (Examples 2 and 3) provide both increased percent ethylene oxide, an indication of increased activity, and increased efficiency relative to a non-cobalt-containing catalyst (Example 1), particularly after longer periods of time on stream. Thus, the inclusion of cobalt in the catalyst can provide for increased activity and/or increased efficiency of an ethylene oxide production catalyst.

Examples 4–6

The preparation technique for the catalyst of Example 4 (comparative) is as follows. For the first impregnation, 59.57 weight parts of Carrier V is placed in an impregnation vessel. The vessel is evacuated and 186.3 weight parts of stock silver solution (Type C) is added. The solution is allowed to contact the carrier for 30 minutes at atmospheric pressure and is then allowed to drain from the carrier for 15 minutes. The first impregnated carrier is calcined in air on a belt roaster using the following procedure. The first impregnated carrier is spread out in a single layer and transported on a stainless steel belt through a 2 in. by 2 in. square heating zone in 2.5 minutes. Hot air, heated externally by a tubular furnace, is discharged from a port immediately below the belt at about 500° C. at a rate of 66 standard cubic feet per hour per square inch. The roasted carrier is then returned to the impregnation vessel for the second impregnation. The solution for the second impregnation is prepared by adding 5.42 weight parts of an aqueous $KNO_3$ solution (6.96% potassium by weight) to 186.3 weight parts of stock silver solution (Type C) while stirring vigorously. The second impregnation is carried out and the resulting second impregnated carrier is calcined again, both second impregnating and calcining processes being conducted in the manner described above.

The catalyst of Example 5 (comparative) is prepared in the following manner. For the first impregnation, 18.33 weight parts of Carrier V is placed in a glass impregnation vessel. The vessel is evacuated and 58.88 weight parts of stock silver solution (Type A) is introduced. The solution is allowed to contact the carrier for 30 minutes at atmospheric pressure and is then allowed to drain from the carrier for 15 minutes. The first impregnated carrier is calcined in air on a belt roaster at 500° C. for 2.5 minutes. The roasted carrier is thereupon returned to the impregnation vessel for the second impregnation. The solution for the second impregnation is prepared by adding 0.321 weight parts of $KNO_3$ to 55.94 weight parts of stock silver solution (Type A) while stirring vigorously. Then 0.0358 weight parts of $KMnO_4$ as an aqueous distilled water solution containing about 3.45 wt % of $KMnO_4$ are added to the impregnating solution. This solution is used promptly after manganese addition for the second impregnation and the resulting second impregnated carrier is calcined again in the manner described earlier.

The catalyst of Example 6 is prepared as follows. For the first impregnation, 59.39 weight parts of Carrier V is placed in an impregnation vessel. The vessel is evacuated and 192.9 weight parts of stock silver solution (Type A) is added. The solution is allowed to contact the carrier for 30 minutes at atmospheric pressure and is then allowed to drain from the carrier for 15 minutes. The first impregnated carrier is calcined in air on a belt roaster at 500° C. for 2.5 minutes. The roasted carrier is then returned to the impregnation vessel for the second impregnation. The solution for the second impregnation is prepared by adding 1.07 weight parts of $KNO_3$ to 167.5 weight parts of stock silver solution (Type A) while stirring vigorously. 0.20 weight parts of $CO(NO_3)_2.6H_2O$ (as a 3.9% by weight solution in distilled water) and 0.12 weight parts of $KMnO_4$ (as a 2.3% by weight solution in distilled water) are added to the impregnating solution. The second impregnation is carried out promptly after manganese and cobalt addition and the resulting second impregnated carrier is calcined again, both second impregnating and second calcining processes being conducted in the manner described above.

These catalysts are evaluated in standard backmixed autoclaves in the following manner. Approximately 40 cc of each catalyst are tested at a nominal gas space velocity of 16000 $hr^{-1}$ with the following feed gas composition: 8 volume % oxygen, 30 volume % ethylene, about 5 ppmw ethyl chloride, about 6 ppmw nitric oxide, and the balance nitrogen. The catalysts are initially operated at 240° C. and the temperature is raised to 255° C. on the following day. The concentrations of ethyl chloride and nitric oxide are adjusted as necessary to optimize the combination of activity and efficiency. After 16 days of testing all three catalysts operate with the same efficiency, within experimental error. However, while the catalysts of Examples 5 and 6 have identical activities, again within experimental error, the catalyst of Example 4 is less active, producing approximately 53% as much ethylene oxide as the other two catalysts.

Examples 7 and 8

The catalyst of Example 7 is prepared using the following procedure. A silver solution is prepared by mixing 17.17 weight parts of ethylenediamine with 19.24 weight parts of distilled water. Then 17.20 weight parts of oxalic acid dehydrate is slowly added to the mixture at ambient conditions. The addition of oxalic acid dehydrate is at a rate such that the exotherm does not cause the temperature of the solution to rise above 40° C. Then 30.12 weight parts of silver oxide is added followed by 6.02 weight parts of monoethanolamine. An additional 2.98 weight parts of distilled water are then added to the solution.

The first impregnation is carried out by placing 9.68 weight parts of Carrier U in an impregnation vessel which is then evacuated to about 35 mm-Hg absolute at ambient temperature. A solution containing 9.36 weight parts of the above-prepared silver solution diluted by the addition of 14.12 weight parts of distilled water is thereupon introduced to the impregnation vessel and allowed to contact the carrier for 30 minutes. The vessel is then opened and the solution is allowed to drain from the carrier for 30 minutes.

The first impregnated carrier is then roasted in hot air using a belt roaster. The first impregnated carrier is spread out in a single layer on an endless stainless steel belt and transported through a heating zone in 5 minutes. Hot air, heating externally by a tubular furnace, is discharged from a port immediately below the belt at about 300° C. at a rate of about 66 standard cubic feed per hour per square inch.

After roasting, 4.64 weight parts of the first impregnated carrier are returned to an impregnation vessel and placed under vacuum. A second impregnating solution is prepared from 13.65 weight parts of the above-prepared silver solution to which are added 0.529 weight parts of an aqueous $Cs_2MoO_4$ solution (1.48% Cs by weight) and 0.060 weight parts of an aqueous $Cs_2SO_4$ solution (6.58% Cs by weight). 0.0042 weight parts of $CoSO_4.7H_2O$ (as a 0.49% by weight solution in distilled water) is then promptly added to the second impregnating solution, which is thereupon added to the evacuated impregnation vessel. The solution is allowed to contact the carrier for 40 minutes and is then drained. The second impregnated carrier is then calcined twice in hot air using a belt roaster. For each pass, the carrier is spread out in a single layer on a 2.625 inch wide endless stainless steel belt (spiral weave) and transported through a 2 inch by 2 inch square heating zone in 2.5 minutes. Hot air, heated externally by a tubular furnace is discharged from a 2 inch by 2 inch port immediately below the belt at about 300° C. at a rate of 66 standard cubic feet per hour per square inch.

The catalyst of Example 8 (comparative) is prepared in a similar manner. A silver solution containing 8.58 weight parts ethylenediamine, 9.62 weight parts distilled water, 8.60 weight parts oxalic acid dihydrate, 15.06 weight parts silver oxide, and 3.01 weight parts monoethanolamine is made following the procedure described above. For the first impregnation, 41.1 weight parts of Carrier U are placed in an impregnation vessel which is then evacuated. A solution containing 49.96 weight parts of the above-prepared silver solution diluted with 67.43 weight parts of distilled water is introduced to the vessel and allowed to contact the carrier for 30 minutes. The vessel is then opened and the solution is allowed to drain from the carrier for 20 minutes. The impregnated carrier is then calcined at 300° C. for 5 minutes on a belt roaster and returned to the impregnation vessel. For the second impregnation, 5.26 weight parts of a $Cs_2MoO_4$ solution (1.47% Cs by weight) and 0.59 weight parts of a $CsSO_4$ solution (6.58% Cs by weight) are mixed with 135.99 weight parts of the undiluted silver solution and then added to the evacuated vessel. After 30 minutes, the vessel is drained and the second impregnated catalyst is roasted at 300° C. for 5 minutes.

Testing of the catalysts of Examples 7 and 8 is conducted in standard backmixed autoclave reactors. Approximately 40 cc of each catalyst is tested at a nominal gas space velocity of 8000 $hr^{-1}$ using a feed gas mixture of 8 volume % oxygen, 30 volume % ethylene, 6.5 volume % carbon dioxide, 0.5 volume % ethane, 2 ppmw ethyl chloride, and the balance nitrogen. In Example 7, the outlet concentration of ethylene oxide at an operating temperature of 251° C. is 2.0 volume %, with an efficiency of 76.4%. For Example 8, an outlet concentration of 2.0 volume % ethylene oxide is reached at a temperature of 251° C. with an efficiency of 80.7%.

Examples 9–11

The preparation technique for catalysts used in Examples 9–11 is as follows.

A silver-containing solution with the following composition is prepared:

16.12 weight parts ethylenediamine,
33.88 weight parts water,
16.37 weight parts oxalic acid,
27.98 weight parts silver oxide, and
5.65 weight parts monoethanolamine.

A cesium perrhenate standard solution containing 0.0060. grams of cesium and 0.0083 grams of rhenium per gram of solution is prepared by adding cesium hydroxide solution and ammonium perrhenate to distilled water. A cesium sulfate standard solution containing 0.015 grams of cesium per gram of solution is prepared by adding cesium sulfate to distilled water. A cesium hydroxide standard solution containing 0.0472 grams of cesium per gram of solution is prepared by adding a concentrated cesium hydroxide solution to distilled water.

The impregnating solution for the catalyst of Example 9 is prepared by adding about 1.31 grams of the standard cesium sulfate solution and 2.7 grams of the standard cesium perrhenate solution to 35 cc of the silver-containing solution. The cesium perrhenate standard solution is heated to 75° C. to assure that the salt is dissolved, and the impregnating solution is warmed to 40° C. to assure that cesium perrhenate is dissolved. The solution is then diluted with distilled water to a final volume of 39 cc.

The impregnating solutions for the catalysts of Example 10 and 11 are prepared by adding about 1.31 grams of the standard cesium sulfate solution and 2.7 grams of the standard cesium perrhenate solution to 35 cc of the silver-containing solution. The cesium perrhenate standard solution is heated to 75° C. to assure that the salt is dissolved, and the impregnating solution is warmed to 40° C. to assure that cesium perrhenate is dissolved. The solution is then diluted with distilled water to a final volume of 39 cc. For the catalyst of Example 10, about 0.0308 grams of cobalt nitrate is added and for the catalyst of Example 11, 0.0308 grams of cobalt nitrate and 0.135 grams of cesium hydroxide standard solution are added.

The catalysts are prepared as follows. Ten grams of carrier N are added to a Pyrex impregnating chamber. The pressure of the chamber is reduced to about 2.0 mm–5.0 mm Hg. The impregnating solution is slowly added to the chamber. The pressure of the chamber is allowed to rise back to atmospheric. The impregnating solution is drained after 20 minutes. The drained solution is retained in a covered beaker. The impregnated carrier is calcined in a roaster at 500° C. for 3 minutes. The impregnating and calcining steps are repeated using the drained solution for impregnation.

The calculated compositions of the catalysts are summarized in the table below:

| Example No. | Ag wt. % | Cs ppm | S ppm | Re ppm | Co ppm |
|---|---|---|---|---|---|
| 9 (Comparative) | 30.2 | 863 | 57 | 544 | — |
| 10 | 30. | 863 | 57 | 544 | 150 |
| 11 | 30. | 1013 | 57 | 544 | 150 |

The catalysts are evaluated in microreactors. Catalyst pills are crushed with a mortar and pestle and screened to the desired size (30–70 mesh). Two grams of crushed catalyst are loaded into a ¼ inch diameter by 5½ inch long stainless steel tube. The tube is placed inside a test oven and connected to a feed system. The temperature of the oven is controlled by a temperature controller and the reactor outlet pressure is controlled at 150 psig with a Groves back pressure regulator. The feed composition is 10 volume percent ethylene, 6 volume percent oxygen, and 5 volume percent carbon dioxide. Nitrogen is the ballast gas. Ethane and ethyl chloride concentrations are given in the table below and are varied to optimize catalyst activity and efficiency. The gas below is adjusted to give a gas space velocity of 4000 hr$^{-1}$.

The performance of these catalysts is summarized in the table below:

| Day | Ethyl Chloride ppm | Example 9 (Comparative) | | | | Example 10 | | | Example 11 | | |
|---|---|---|---|---|---|---|---|---|---|---|---|
| | | Ethane % | EO % | Eff % | T ° C. | EO % | Eff % | T ° C. | EO % | Eff % | T ° C. |
| 8 | 8.4 | 0.46 | 1.3 | 86.7 | 249 | | | | | | |
| 11 | 11.8 | 0.45 | 1.61 | 85.0 | 259 | | | | | | |
| 6 | 7.7 | 0.44 | | | | 1.39 | 83.6 | 250 | 1.43 | 84.7 | 251 |
| 9 | 8 | 0.44 | | | | 1.74 | 81.2 | 260 | 1.78 | 82.6 | 260 |

These results indicate that the catalysts of Examples 10 and 11, which include cobalt component and rhenium component, provide increased activity relative to the catalyst of Example 9 which includes no cobalt component.

While this invention has been described with respect to various specific examples and embodiments, it is to be understood that the invention is not limited thereto and that it can be variously practiced within the scope of the following claims.

What is claimed is:

1. A catalyst for the manufacture of alkylene oxide by the epoxidation of alkene in the vapor phase in the presence of at least one efficiency-enhancing gaseous member of a redox-half reaction pair, said catalyst comprising silver on an inert, refractory solid support; an efficiency-enhancing amount of at least one efficiency-enhancing salt of a member of a redox-half reaction pair; and about 10 to about 1,000 ppm by weight of cobalt component to enhance efficiency stability of the catalyst as compared to a similar catalyst which does not contain the cobalt component, said comparison being under STANDARD ETHYLENE OXIDE PROCESS CONDITIONS.

2. The catalyst of claim 1 in which the cobalt component comprises cobalt cation.

3. The catalyst of claim 1 in which at least about 25 ppmw of cobalt component calculated on the weight of cobalt are present based on the weight of the catalyst.

4. The catalyst of claim 1 in which the efficiency-enhancing salt, calculated as cation, is about 0.01 to about 5 percent by weight based on the total weight of the catalyst.

5. The catalyst of claim 1 in which at least one efficiency-enhancing salt of a member of a redox-half reaction pair comprises alkali metal nitrate.

6. The catalyst of claim 5 in which the alkali metal nitrate comprises at least one of potassium nitrate and rubidium nitrate.

7. The catalyst of claim 6 in which the alkali metal nitrate comprises potassium nitrate.

8. The catalyst of claim 7 in which the efficiency-enhancing salt, calculated as cation, is about 0.01 to about 5 percent by weight based on the weight of the catalyst.

* * * * *